«12» United States Patent
Kono et al.

«10» Patent No.: US 11,457,876 B2
«45» Date of Patent: Oct. 4, 2022

«54» DIAGNOSIS ASSISTING APPARATUS, STORAGE MEDIUM, AND DIAGNOSIS ASSISTING METHOD FOR DISPLAYING DIAGNOSIS ASSISTING INFORMATION IN A REGION AND AN ENDOSCOPIC IMAGE IN ANOTHER REGION

«71» Applicant: OLYMPUS CORPORATION, Tokyo (JP)

«72» Inventors: Takashi Kono, Hachioji (JP); Yamato Kanda, Hino (JP); Katsuyoshi Taniguchi, Hino (JP); Makoto Kitamura, Hachioji (JP)

«73» Assignee: OLYMPUS CORPORATION, Tokyo (JP)

«*» Notice: Subject to any disclaimer, the term of this patent is extended or adjusted under 35 U.S.C. 154(b) by 138 days.

«21» Appl. No.: 17/032,765

«22» Filed: Sep. 25, 2020

«65» Prior Publication Data

US 2021/0113159 A1 Apr. 22, 2021

Related U.S. Application Data

«63» Continuation of application No. PCT/JP2018/013767, filed on Mar. 30, 2018.

«51» Int. Cl.
*A61B 5/00* (2006.01)
*G06K 9/62* (2022.01)
(Continued)

«52» U.S. Cl.
CPC .......... *A61B 5/7282* (2013.01); *A61B 1/0005* (2013.01); *A61B 1/00006* (2013.01);
(Continued)

«58» Field of Classification Search
CPC . A61B 5/7282; A61B 1/00006; A61B 1/0005; A61B 5/1079; A61B 5/7275;
(Continued)

«56» References Cited

U.S. PATENT DOCUMENTS

2017/0091582 A1\* 3/2017 Takata ................. G06V 10/758
2017/0200268 A1\* 7/2017 Podilchuk ............ G06K 9/6278
(Continued)

FOREIGN PATENT DOCUMENTS

JP 2006-115921 A 5/2006
JP 4651353 B2 3/2011
(Continued)

OTHER PUBLICATIONS

International Search Report dated Jun. 26, 2018 received in PCT/JP2018/013767.
(Continued)

*Primary Examiner* — Siamak Harandi
«74» *Attorney, Agent, or Firm* — Scully, Scott, Murphy & Presser, P.C.

«57» ABSTRACT

A diagnosis assisting apparatus includes a processor. The processor is configured to detect at least one target region from an acquired image and output position information of the target region. The processor is also configured to classify the target region based on predetermined classification conditions corresponding to diagnosis indices and output diagnosis assisting information indicating a degree of seriousness of the target region. The processor is then configured to control a display image such that a first period, during which the diagnosis assisting information is displayed in a first region, is different from a second period, during which the position information is superimposed on the image in a second region and is displayed.

29 Claims, 6 Drawing Sheets (51) Int. Cl.
*A61B 34/20* (2016.01)
*G06T 7/62* (2017.01)
*G06T 7/70* (2017.01)
*G16H 50/20* (2018.01)
*G16H 30/40* (2018.01)
*A61B 1/00* (2006.01)
*A61B 5/107* (2006.01)
*G06T 7/00* (2017.01)
*G06T 7/20* (2017.01)
*G06T 11/00* (2006.01)

(52) U.S. Cl.
CPC .......... *A61B 5/1079* (2013.01); *A61B 5/7275* (2013.01); *A61B 34/20* (2016.02); *G06K 9/6267* (2013.01); *G06T 7/0012* (2013.01); *G06T 7/20* (2013.01); *G06T 7/62* (2017.01); *G06T 7/70* (2017.01); *G06T 11/00* (2013.01); *G16H 30/40* (2018.01); *G16H 50/20* (2018.01); *A61B 5/7267* (2013.01); *A61B 2034/2065* (2016.02); *G06T 2207/30096* (2013.01); *G06V 2201/034* (2022.01)

(58) Field of Classification Search
CPC .................. A61B 34/20; A61B 5/7267; A61B 2034/2065; A61B 1/000094; A61B 5/0084; A61B 1/045; G06K 9/6267; G06K 9/6277; G06T 7/0012; G06T 7/20; G06T 7/62; G06T 7/70; G06T 11/00; G06T 2207/30096; G16H 30/40; G16H 50/20; G06V 2201/034; G06V 2201/03; G06V 10/255

See application file for complete search history.

(56) References Cited

U.S. PATENT DOCUMENTS

2018/0249900 A1   9/2018  Imaizumi et al.
2019/0239718 A1*  8/2019  Iwaki ................ G02B 23/2461

FOREIGN PATENT DOCUMENTS

| JP | 2011-255006 A | 12/2011 |
| JP | 2016-067706 A | 5/2016 |
| JP | 2017-213097 A | 12/2017 |
| WO | 2016/199273 A1 | 12/2016 |
| WO | 2017/057574 A1 | 4/2017 |
| WO | 2017/081976 A1 | 5/2017 |
| WO | 2017/203560 A1 | 11/2017 |

OTHER PUBLICATIONS

Japanese Office Action dated Jun. 8, 2021 received in 2020-508824.

* cited by examiner

DIAGNOSIS ASSISTING APPARATUS, STORAGE MEDIUM, AND DIAGNOSIS ASSISTING METHOD FOR DISPLAYING DIAGNOSIS ASSISTING INFORMATION IN A REGION AND AN ENDOSCOPIC IMAGE IN ANOTHER REGION

CROSS REFERENCE TO RELATED APPLICATION

This application is a continuation application of PCT/JP2018/013767 filed on Mar. 30, 2018, the entire contents of which are incorporated herein by this reference.

BACKGROUND OF THE INVENTION

1. Field of the Invention

The present invention relates to a diagnosis assisting apparatus, a storage medium, and a diagnosis assisting method.

2. Description of the Related Art

As a conventional technique, there is a diagnosis assisting apparatus that analyzes a medical image and displays the analysis result to assist doctors with diagnosis. For example, Japanese Patent Application Laid-Open Publication No. 2006-115921 discloses a diagnosis assisting apparatus configured to display a medical image for diagnosis during the diagnosis by a doctor in order to find all abnormal regions without discouraging the doctor from reading an image and to superimpose and display a medical image in which a marker is attached to a lesion candidate by analysis and a medical image in which an annotation is recorded by the doctor, after the doctor's diagnosis is completed.

SUMMARY OF THE INVENTION

A diagnosis assisting apparatus according to an aspect of the present invention includes a processor configured to detect at least one target region from an acquired image and output position information of the target region, classify the target region based on a predetermined classification condition corresponding to a diagnosis index and output diagnosis assisting information indicating a degree of seriousness of the target region, and control a display image such that a first period, during which the diagnosis assisting information is displayed, has a period that does not overlap with a second period, during which the position information is superimposed on the image and is displayed.

A storage medium according to another aspect of the present invention is a non-transitory computer-readable storage medium in which a program is stored, the program including: a code configured to detect a target region from an acquired image and output position information of the target region; a code configured to classify the target region based on a predetermined classification condition corresponding to a diagnosis index and output diagnosis assisting information indicating a degree of seriousness of the target region; and a code configured to control a display image such that a first period, during which the diagnosis assisting information is displayed in a first region, has a period that does not overlap with a second period, during which the position information is superimposed on the image in a second region and is displayed.

A diagnosis assisting method according to further another aspect of the present invention includes: detecting a target region from an acquired image and outputting position information of the target region; classifying the target region based on a predetermined classification condition corresponding to a diagnosis index and outputting diagnosis assisting information indicating a degree of seriousness of the target region; and controlling a display image such that a first period, during which the diagnosis assisting information is displayed in a first region, has a period that does not overlap with a second period, during which the position information is superimposed on the image in a second region and is displayed.

DETAILED DESCRIPTION OF THE PREFERRED EMBODIMENTS

Embodiments of the present invention will be described below with reference to the drawings.

(Configuration of First Embodiment)

Figure 1:
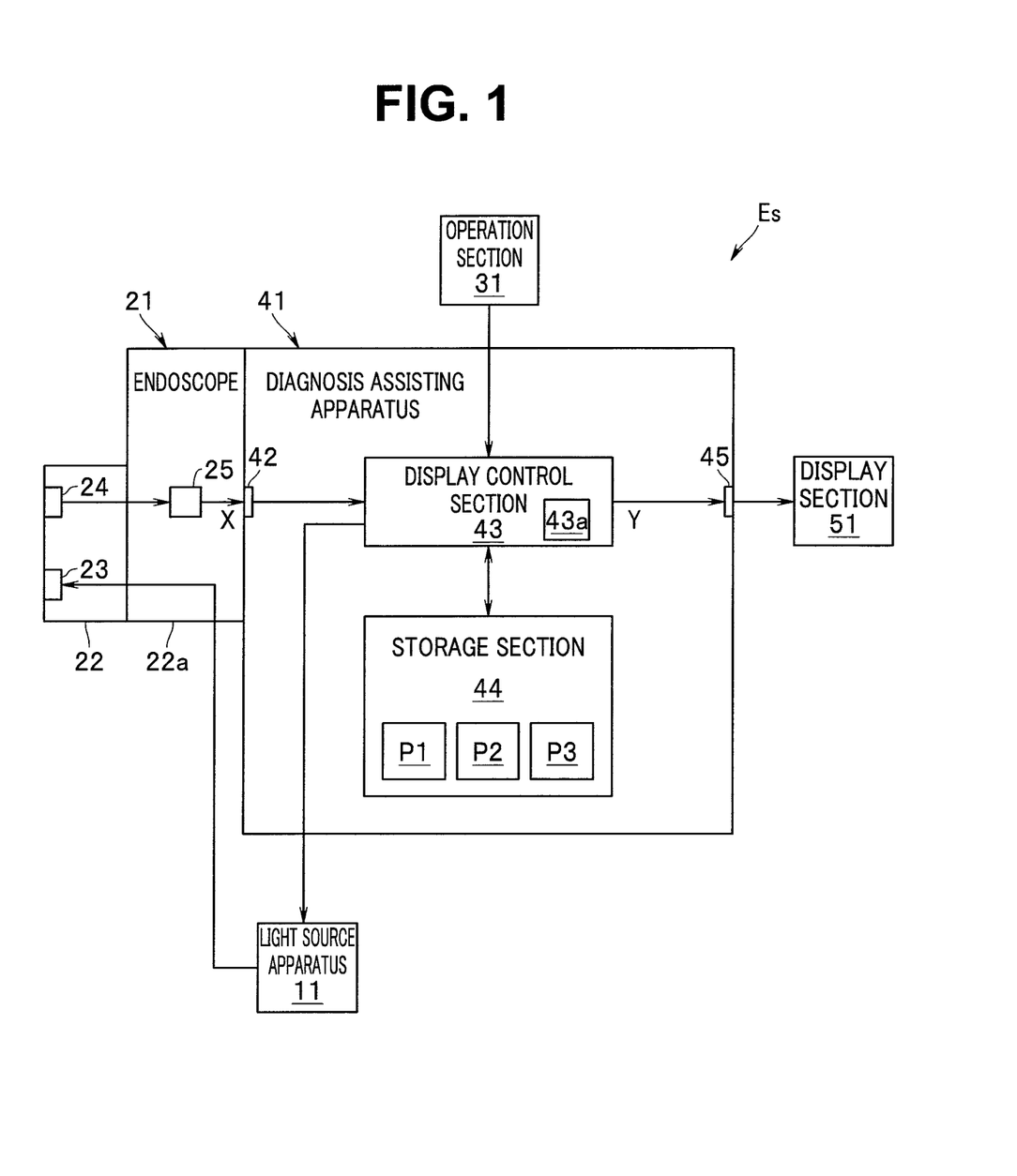
FIG. 1 is a block diagram showing an example of a configuration of a diagnosis assisting apparatus according to a first embodiment of the present invention.
Figure 2:
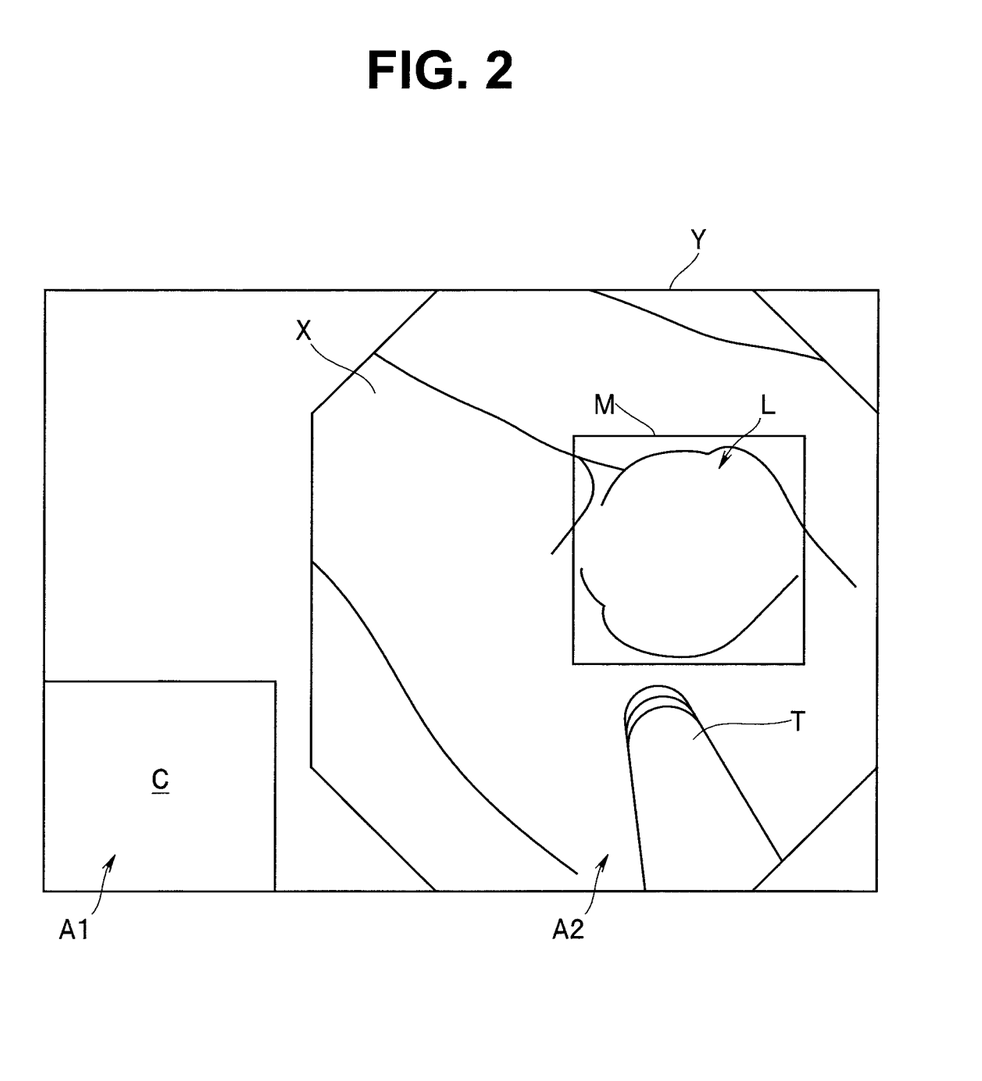
FIG. 2 is an explanatory diagram illustrating an example of a display image of the diagnosis assisting apparatus according to the first embodiment of the present invention.

FIG. 1 is a block diagram showing an example of a configuration of an endoscope system Es according to a first embodiment of the present invention. FIG. 2 is an explanatory diagram for explaining an example of a display image Y of a diagnosis assisting apparatus 41 according to the first embodiment of the present invention.

An endoscope system Es includes a light source apparatus 11, an endoscope apparatus 21, an operation section 31, a diagnosis assisting apparatus 41, and a display section 51. The light source apparatus 11 is connected to each of the endoscope apparatus 21 and the diagnosis assisting apparatus 41. The endoscope apparatus 21 is connected to the diagnosis assisting apparatus 41. The operation section 31 is connected to the diagnosis assisting apparatus 41. The diagnosis assisting apparatus 41 is connected to the display section 51.

The light source apparatus 11 outputs illumination light such as white light or narrow-band light to the endoscope apparatus 21 under control of the diagnosis assisting apparatus 41.

The endoscope apparatus 21 is configured to pick up an image of an inside of a subject. The endoscope apparatus 21 includes an endoscope 22, an illumination section 23, an image pickup section 24, and an image processing section 25.

The endoscope 22 is formed in an elongated shape to be capable of being inserted into the subject. The endoscope 22 includes various conduits and signal lines (which are not shown) therein. The endoscope 22 includes a bending mechanism (not shown) and bends according to instructions inputted by an operator.

A control unit 22a is provided at a proximal end portion of the endoscope 22. The control unit 22a is connected to the diagnosis assisting apparatus 41.

The illumination section 23 is provided at a distal end portion of the endoscope 22 and irradiates the subject with the illumination light inputted from the light source apparatus 11.

The image pickup section 24 is provided at the distal end portion of the endoscope 22. The image pickup section 24 is configured by an image pickup device such as a CMOS sensor or a CCD. The image pickup section 24 is configured to pick up an image of the subject illuminated by the illumination section 23, and to output an image pickup signal to the image processing section 25.

The image processing section 25 is provided in the control unit 22a. The image processing section 25 performs image processing such as gain adjustment, white balance adjustment, gamma correction, contour enhancement correction, or enlargement/reduction adjustment on the image pickup signal inputted from the image pickup section 24 to generate an endoscope image X, and outputs the generated image to the diagnosis assisting apparatus 41. All or some of the image processing performed by the image processing section 25 may be configured to be performed in the diagnosis assisting apparatus 41.

The operation section 31 is connected to the diagnosis assisting apparatus 41. Through the operation section 31, various instructions, for example, bending of the endoscope 22, switching of the illumination light to be irradiated from the illumination section 23, a release operation, and a freeze operation can be inputted. In addition, through the operation section 31, various instructions, for example, start and end of a diagnosis assisting process and start and end of information display of diagnosis assisting information C and mark M (see FIG. 2) can be inputted. The operation section 31 is connected to a display control section 43 of the diagnosis assisting apparatus 41, and outputs to the display control section 43 an instruction signal corresponding to the instruction input. The operation section 31 may be provided in the endoscope apparatus 21, the diagnosis assisting apparatus 41, or the display section 51.

The diagnosis assisting apparatus 41 is an apparatus configured to generate a display image Y based on the endoscope image X and output the generated image. The diagnosis assisting apparatus 41 includes an input section 42, a display control section 43, a storage section 44, and an output section 45.

The input section 42 is a circuit used to connect the endoscope apparatus 21 to the display control section 43. The input section 42 is connected to the endoscope apparatus 21 and the display control section 43, sequentially receives endoscope images X from the image processing section 25 of the endoscope apparatus 21, and outputs the endoscope images X to the display control section 43.

The display control section 43 is a circuit configured to control the respective sections in the endoscope system Es. The display control section 43 includes a processor 43a. A function of the display control section 43 is realized by a plurality of circuits in which the processor 43a reads and executes programs and various types of information stored in the storage section 44.

Further, the display control section 43 detects the amount of gain adjustment or brightness of the endoscope image X, outputs a control signal, and controls the amount of light emitted from the light source apparatus 11.

In addition, the display control section 43 generates a display image Y based on the endoscope image X, and outputs the generated image to the output section 45. As shown in FIG. 2, the display image Y includes a first region A1 used to display the diagnosis assisting information C, and a second region A2 which is a region different from the first region A1 and used to display the endoscope image X and position information of a target region L.

The position information is displayed by, for example, the mark M surrounding the target region L on the endoscope image X. The position information is not limited to the mark M, but may be displayed by an arrow image or another image such as an icon.

The display control section 43 controls the display image Y to set a first period, during which the diagnosis assisting information C is displayed in the first region A1, and a second period, during which the position information is superimposed on the endoscope image X and is displayed in the second region A2, to be different from each other.

The storage section 44 includes a non-transitory computer-readable storage medium configured to store a readable/writable program such as a RAM, a ROM, a flash ROM, an HDD, or an SSD.

The storage section 44 stores various types of data and various programs used to control the endoscope system Es, and also stores programs of a detection portion P1, a classification portion P2, and a period setting portion P3.

In addition, the storage section 44 stores model information used for matching in the detection portion P1 and a predetermined classification condition used in the classification portion P2. The predetermined classification condition can be determined in advance to classify the target region L based on NICE classification that classifies the degree of seriousness of tumor, for example. The storage section 44 is also used as a working memory configured to temporarily store information such as the endoscope image X.

The output section 45 is a circuit used to connect the display section 51 to the display control section 43. The output section 45 outputs the display image Y generated by the display control section 43 to the display section 51.

The display section 51 includes a display panel such as an LCD and an OLED. The display section 51 is connected to the output section 45 and displays the display image Y inputted from the output section 45. The display section 51 may be connected to the diagnosis assisting apparatus 41 by wireless communication.

(Configuration of Program Used for Diagnosis Assisting Process)

Subsequently, the detection portion P1, the classification portion P2, and the period setting portion P3 will be described. The detection portion P1, the classification portion P2, and the period setting portion P3 are programs used for the diagnosis assisting process of the diagnosis assisting apparatus 41.

Through a predetermined detection process, the detection portion P1 detects the target region L from the endoscope image X acquired by the endoscope apparatus 21, and outputs the position information of the target region L. In the predetermined detection process, for example, a contour is extracted from the amount of change in pixel values in pixels adjacent to each other by a predetermined contour extraction process, and the target region L is detected by matching with the model information read from the storage section 44. The position information is, for example, coordinates of a center of the target region L. The detection portion P1 may also detect a plurality of target regions L from the endoscope image X.

Further, the detection portion P1 detects a size of the target region L through the predetermined detection process. The size of the target region L indicates, for example, information on a distance between the center and an outer edge of the target region L.

The detection portion P1 also detects a treatment instrument T from the endoscope image X through the predetermined detection process, and also outputs position information of the treatment instrument T (see FIG. 2).

The processing of the detection portion P1 may be performed by, for example, calculation of a color and a spatial frequency of the endoscope image X without being limited to the processes described above, or may include a process of detecting the target region L with an arithmetic apparatus using an artificial intelligence technique such as machine learning.

The classification portion P2 classifies the target region L based on predetermined classification conditions corresponding to diagnosis indices, and outputs the diagnosis assisting information C indicating the degree of seriousness of the target region L. The predetermined classification conditions include, for example, classification conditions based on NICE classification and reference images. The diagnosis assisting information C may include probabilities of an adenomatous lesion and a non-adenomatous lesion, respectively.

The classification portion P2 extracts an image of the target region L when the target region L is inputted from the detection portion P1. The classification portion P2 detects a color tone based on a luminance value of the extracted image. Through a predetermined contour extraction process, the classification portion P2 detects a blood vessel pattern and a surface pattern based on the extracted image. The classification portion P2 compares detection results with the predetermined classification conditions, calculates a conformity rate of each of Type1 to Type3 through a predetermined arithmetic operation, and generates the diagnosis assisting information C. The display control section 43 displays the diagnosis assisting information C in the first region A1 of the display image Y during the first period.

The processing of the classification portion P2 may be performed by an arithmetic apparatus using an artificial intelligence technique without being limited to the processes described above.

Figure 3:
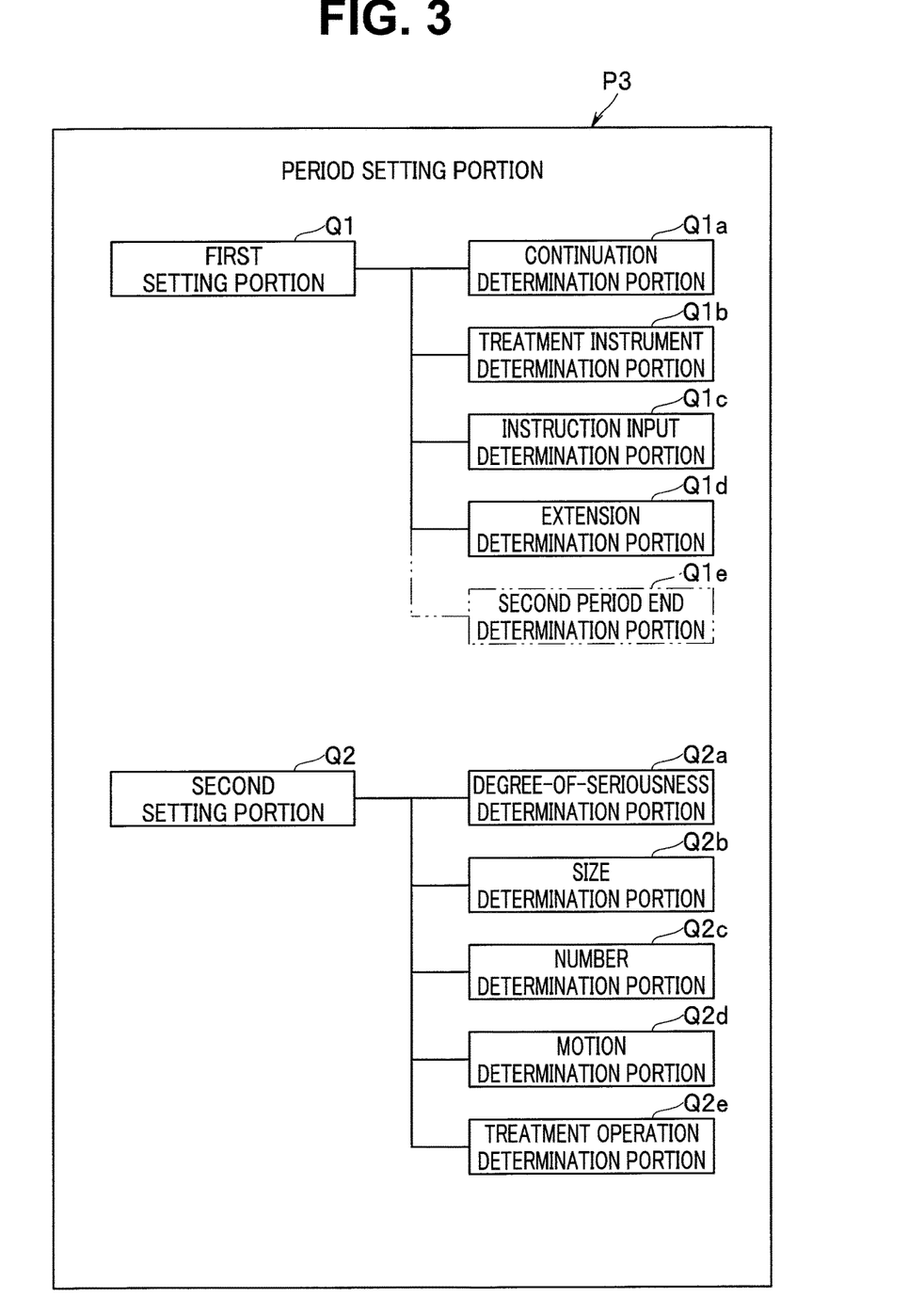
FIG. 3 is a block diagram showing an example of a configuration of a period setting portion of the diagnosis assisting apparatus according to the first embodiment of the present invention.

FIG. 3 is a block diagram showing an example of a configuration of the period setting portion P3 of the diagnosis assisting apparatus 41 according to the first embodiment of the present invention.

The period setting portion P3 sets each of the first period and the second period such that the first period and the second period are different from each other. More specifically, the period setting portion P3 sets each of the first period and the second period such that the first period has a period that does not overlap with the second period. The period setting portion P3 includes a first setting portion Q1 and a second setting portion Q2.

The first setting portion Q1 sets the first period. More specifically, the first setting portion Q1 sets a first start time point Cs at which the first period starts and a first end time point Ce at which the first period ends. As shown in FIG. 3, the first setting portion Q1 includes a continuation determination portion Q1a, a treatment instrument determination portion Q1b, an instruction input determination portion Q1c, and an extension determination portion Q1d.

The continuation determination portion Q1a determines based on the detection result of the detection portion P1 whether the target region L is continuously detected. For example, the continuation determination portion Q1a compares respective frames of the sequentially-acquired endoscope image X with each other, and determines whether the target region L continuously appears on the frames. When the continuation determination portion Q1a determines that the target region L is continuously detected, the first setting portion Q1 sets the first start time point Cs with predetermined control information such as a current time point, and starts the first period. When the first period starts, the display control section 43 displays the diagnosis assisting information C on the display image Y. On the other hand, when the continuation determination portion Q1a determines that the target region L is not continuously detected, the first setting portion Q1 sets the first end time point Ce with predetermined control information, and ends the first period. When the first period ends, the display control section 43 does not display the diagnosis assisting information C on the display image Y. In other words, the first setting portion Q1 sets a period, during which the target region L is continuously detected, as the first period.

The treatment instrument determination portion Q1b determines based on the detection result of the detection portion P1 whether the treatment instrument T is detected. The processing of the treatment instrument determination portion Q1b is performed within the first period. When the treatment instrument T is detected by the treatment instrument determination portion Q1b, the first setting portion Q1 sets the first end time point Ce with predetermined control information, and ends the first period. In other words, when the treatment instrument T is detected in the endoscope image X, the first setting portion Q1 sets the end of the first period.

The instruction input determination portion Q1c determines based on the instruction signal inputted from the operation section 31 whether any instruction to start or end an information display from the diagnosis assisting information C and the mark M exists. When the instruction input determination portion Q1c determines that an instruction signal for the start of the information display exists, the first setting portion Q1 sets the first start time point Cs with predetermined control information, and starts the first period. On the other hand, when the instruction input determination portion Q1c determines that an instruction signal for the end of the information display exists, the first setting portion Q1 sets the first end time point Ce with predetermined control information, and ends the first period. In other words, the first setting portion Q1 sets at least one of the start and end of the first period in response to the instruction input from the operator.

The extension determination portion Q1d determines a difference between the first end time point Ce and a second end time point Me. More specifically, the extension determination portion Q1d determines whether the difference between the end time point of the first period and the end time point of the second period is smaller than a predetermined difference. When it is determined that the difference is smaller than the predetermined difference, the first setting portion Q1 extends the first period by a predetermined extension time such that the diagnosis assisting information C can be easily seen. The predetermined extension time is empirically or experimentally determined in advance.

The second setting portion Q2 sets the second period according to the setting of the first period. More specifically, the second setting portion Q2 sets a second start time point Ms at which the second period starts and a second end time point Me at which the second period ends according to the setting of the first period and the diagnosis assisting information C. The second setting portion Q2 includes a degree-of-seriousness determination portion Q2a, a size determination portion Q2b, a number determination portion Q2c, a motion determination portion Q2d, and a treatment operation determination portion Q2e.

The degree-of-seriousness determination portion Q2a determines the degree of seriousness based on the diagnosis assisting information C outputted from the classification portion P2. When the classification portion P2 outputs the diagnosis assisting information C having the probability of the adenomatous lesion and the probability of the non-adenomatous lesion, the degree-of-seriousness determination portion Q2a determines based on the probability that the target region L is either the adenomatous lesion or the non-adenomatous lesion. For example, when the probability of the adenomatous lesion is equal to or higher than a predetermined degree, the degree-of-seriousness determination portion Q2a determines that the target region L is an adenomatous lesion. When the probability of the non-adenomatous lesion is equal to or higher than the predetermined degree, the degree-of-seriousness determination portion Q2a determines that the target region L is a non-adenomatous lesion. When the target region L is determined to be the non-adenomatous lesion, the second setting portion Q2 sets the second period longer than when the target region L is determined to be the adenomatous lesion, such that the target region L with higher degree of seriousness can be observed longer. The length of the second period of the non-adenomatous lesion and the length of the second period of the adenomatous lesion are empirically or experimentally determined in advance. Similarly, in the size determination portion Q2b, the number determination portion Q2c, and the motion determination portion Q2d to be described below, the length of the second period corresponding to the determination result is empirically or experimentally determined in advance.

For example, in a case where the second period is preset to 1 second when it is determined to be the adenomatous lesion and the second period is preset to 2 seconds when it is determined to be the non-adenomatous lesion, the second setting portion Q2 determines the second start time point Ms and the second end time point Me such that a length of the second period is 2 seconds, and sets the second period when the degree-of-seriousness determination portion Q2a determines that the target region L is the non-adenomatous lesion. More specifically, when it is determined to be the non-adenomatous lesion, the second setting portion Q2 sets the second start time point Ms to the same time point as the first start time point Cs, and sets a time point obtained by adding 2 seconds to the second start time point Ms to the second end time point Me.

The size determination portion Q2b determines a size of the target region L detected by the detection portion P1. When the detection portion P1 determines the size of the target region L through the predetermined detection process, the size determination portion Q2b determines whether the size is smaller than a predetermined size. When the size is determined to be smaller than the predetermined size, the second setting portion Q2 sets the second period longer than when the size is determined to be larger than the predetermined size.

Further, the size determination portion Q2b determines whether the size is 5 mm or smaller such that a small target region L can be ignored. When the size is determined to be 5 mm or smaller, the second setting portion Q2 sets the second period.

The second setting portion Q2 may set the second period based on both the determination results of the degree-of-seriousness determination portion Q2a and the size determination portion Q2b. For example, when the target region L is the adenomatous lesion and the size is determined to be smaller than the predetermined size, the second setting portion Q2 may set the second period longer than when the size is determined to be larger than the predetermined size. In other words, the size determination portion Q2b determines the size, and the second setting portion Q2 sets the second period according to the determination result of the size determination portion Q2b.

The number determination portion Q2c determines whether the number of target regions L inputted from the detection portion P1 is larger than a predetermined number. When the number is determined to be larger than the predetermined number, the second setting portion Q2 sets the second period longer than when the number is determined to be smaller than the predetermined number. In other words, the second setting portion Q2 sets the second period according to the number of target regions L.

In addition, when a plurality of target regions L are present, the second setting portion Q2 sets a different second period for each of the target regions L. When a plurality of target regions L are detected simultaneously by the detection portion P1, the second setting portion Q2 may set the second period for each of the target regions L by shifting the start of the second period by a predetermined time from each other. For example, when three target regions L are detected and the predetermined time is 0.5 seconds, the second setting portion Q2 may set the second period in such a manner as to start the second period of a second target region L after starting the second period of a first target region L after a lapse of 0.5 seconds and as to start the second period of a third target region L after a lapse of 0.5 seconds.

The motion determination portion Q2d determines motion of the target region L detected by the detection portion P1. More specifically, the motion determination portion Q2d determines a motion direction and a motion amount of the target region L in the endoscope image X. The second setting portion Q2 sets the second period according to the motion direction and the motion amount.

For example, the motion determination portion Q2d determines whether the motion amount is larger than a predetermined amount. When the motion amount is determined to be larger than the predetermined amount, the second setting portion Q2 sets the second period longer than when the motion amount is determined to be smaller than the predetermined amount.

Further, when the motion direction is determined to be a direction toward the center of the endoscope image X, the second setting portion Q2 sets the second period longer than when the motion direction is determined to be a direction toward the outside of the endoscope image X.

The treatment operation determination portion Q2e determines whether the treatment instrument T detected by the detection portion P1 performs a predetermined treatment operation. When the predetermined treatment operation is determined to be performed, the second setting portion Q2 sets the end of the second period. The predetermined treatment operation is, for example, an operation in which a snare (not shown) protrudes from a distal end portion of the treatment instrument T. The predetermined treatment operation is not limited to the operation described above, but may be, for example, an operation of bringing the treatment instrument T closer to the target region L, an operation of injecting a fluid from the treatment instrument T to the target region L, an operation of marking the target region L, or an operation of excising the tumor in the target region L.

The first setting portion and the second setting portion may be configured such that determination conditions are preset at the time of shipment from a factory or by the instruction input from the operator. Even in this case, when the first period and the second period are the same, the first setting portion Q1 further delays the first end time point Ce such that the first period has a period that does not overlap with the second period.

For example, the first setting portion Q1 may be preset to start the first period by the detection of the target region L in the detection portion P1, or may be preset to start the first period by the instruction input from the operator, such as a release operation, a freeze operation, or a start of information display.

Further, the first setting portion Q1 may be preset to end the first period by non-detection of the target region L, may be preset to end the first period by the instruction input from the operator, such as cancellation of a release operation, cancellation of a freeze operation, or an end of information display, or may be preset to end the first period by a lapse of a predetermined first time from the first start time point Cs.

The second setting portion Q2 may be preset to start the second period according to the start of the first period, or may be preset to start the second period by the instruction input from the operator.

The second setting portion Q2 may be preset to end the second period by non-detection of the target region L, may be preset to end the second period by the instruction input from the operator, or may be preset to end the second period by a lapse of a predetermined second time from the second start time point Ms.

(Operation)

An operation of the diagnosis assisting apparatus 41 will be described below.

Figure 4:
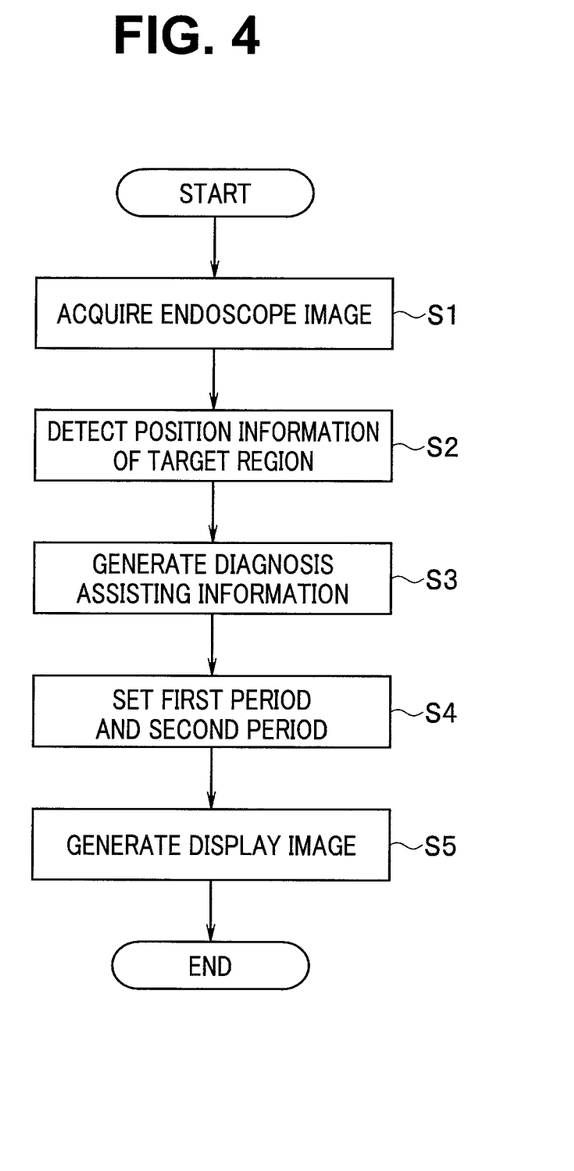
FIG. 4 is a flowchart showing an example of a diagnosis assisting process of the diagnosis assisting apparatus according to the first embodiment of the present invention.

FIG. 4 is a flowchart showing an example of the diagnosis assisting process of the diagnosis assisting apparatus 41 according to the first embodiment of the present invention.

When the instruction to start the diagnosis assisting process is inputted from the operation section 31, the display control section 43 reads a program from the storage section 44, and starts the diagnosis assisting process.

The endoscope image X is acquired (S1). The display control section 43 acquires the endoscope image X, which is acquired by the endoscope apparatus 21 through the input section 42.

The position information of the target region L is detected (S2). The target region L is detected by the predetermined detection process in the detection portion P1, and the position information of the target region L is outputted.

The diagnosis assisting information C is generated (S3). The target region L is classified based on the predetermined classification conditions by the processing of the classification portion P2, and the diagnosis assisting information C indicating the degree of seriousness of the target region L is outputted.

The first period and the second period are set (S4). The first period and the second period are set by the processing of the period setting portion P3 to be different from each other.

The display image Y is generated (S5). The display control section 43 displays the endoscope image X in the second region A2. The display control section 43 displays the diagnosis assisting information C in the first region A1 during the first period. The display control section 43 displays the mark M during the second period so as to surround the target region L of the second region A2.

In other words, a diagnosis assisting program allows a computer to execute a code configured to detect the target region L from the acquired image X through the predetermined detection process and output the position information of the target region L, a code configured to classify the target region L based on the predetermined classification conditions and output the diagnosis assisting information C indicating the degree of seriousness of the target region L, and a code configured to control the display image Y such that the first period, during which the diagnosis assisting information C is displayed in the first region A1, is different from the second period, during which the position information is superimposed on the image X in the second region A2 and is displayed.

In a diagnosis assisting method, the detection portion P1 detects the target region L from the acquired image X through the predetermined detection process and outputs the position information of the target region L, the classification portion P2 classifies the target region L based on the predetermined classification conditions and outputs the diagnosis assisting information C indicating the degree of seriousness of the target region L, and the display control section 43 controls the display image Y such that the first period, during which the diagnosis assisting information C is displayed in the first region A1, is different from the second period, during which the position information is superimposed on the image X in the second region A2 and is displayed.

Figure 5:
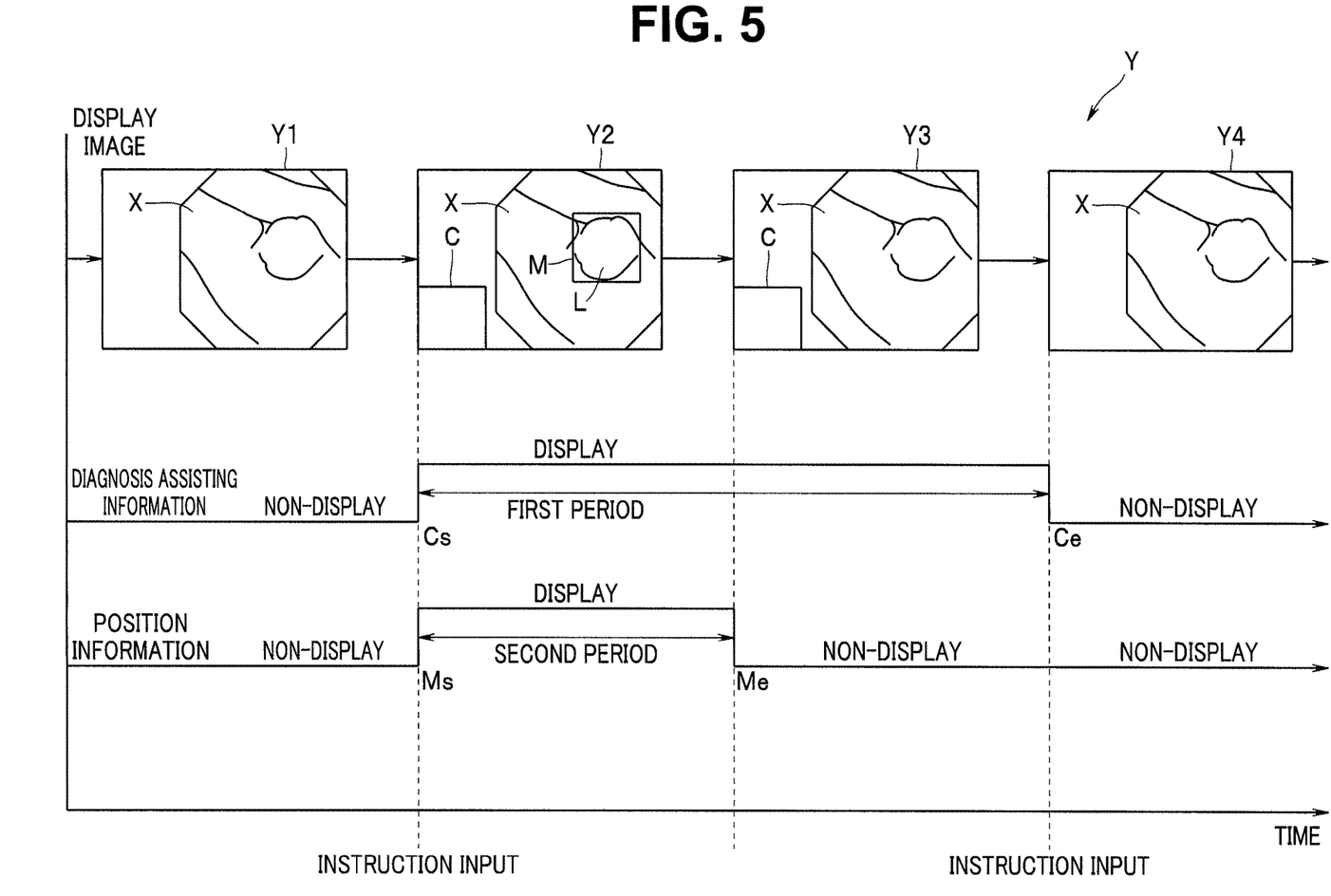
FIG. 5 is an explanatory diagram illustrating an example of a transition of the display image of the diagnosis assisting apparatus according to the first embodiment of the present invention.

FIG. 5 is an explanatory diagram showing an example of a transition of the display image Y of the diagnosis assisting apparatus according to the first embodiment of the present invention.

In FIG. 5, the endoscope image X having the target region L is displayed in the display image Y1. Although the target region L is detected in the diagnosis assisting apparatus 41, the diagnosis assisting information C and the mark M are not displayed on the display image Y1 such that the operator can visually diagnose the target region L.

When the operator inputs an instruction to start an information display through the operation section 31, the instruction input determination portion Q1c determines that the instruction to start the information display is inputted. The first setting portion Q1 sets the start of the first period. The display control section 43 displays the diagnosis assisting information C on a display image Y2 from the first start time point Cs. The second setting portion Q2 sets the start of the second period according to the start of the first period. The display control section 43 displays the mark M on the display image Y2 from the second start time point Ms. The second setting portion Q2 sets the second end time point Me based on the determination results of the degree-of-seriousness determination portion Q2a, the size determination portion Q2b, the number determination portion Q2c, and the motion determination portion Q2d.

At the second end time point Me, the display control section 43 does not display the mark M in a state of displaying the diagnosis assisting information C such that the operator can visually diagnose the diagnosis assisting information C and the endoscope image X. A display image Y3 shows an example in which the diagnosis assisting information C is displayed and the mark M is not displayed.

The operator can allow the diagnosis assisting information C and the mark M not to be displayed after the visual diagnosis is completed. When the operator inputs an instruction to end the information display through the operation section 31, the instruction input determination portion Q1c determines that the instruction to end the information display is inputted, and the first setting portion Q1 sets the end of the first period. As shown in a display image Y4, the display control section 43 displays neither the diagnosis assisting information C nor the mark M at the first end time point Ce. When the extension determination portion Q1d determines that the difference between the first end time point Ce and the second end time point Me is smaller than the predetermined difference, the first setting portion Q1 extends the first period by a predetermined extension time such that the first period has a period that does not overlap with the second period.

In the endoscope system Es, when the target region L is detected, the mark M is displayed on the endoscope image X, and the diagnosis assisting information C is displayed in a region different from the endoscope image X. Subsequently, in the endoscope system Es, the mark M is not displayed in the state where the diagnosis assisting information C is displayed. Thus, the operator can grasp the position of the target region L from the mark M displayed on the endoscope image, can grasp the degree of seriousness of the target region L from the diagnosis assisting information C, and can proceed with the diagnosis. Subsequently, the operator can visually observe the target region L in which the mark M is not displayed, can grasp the degree of seriousness of the target region L from the diagnosis assisting information C, and can proceed with the diagnosis.

According to the first embodiment, the diagnosis assisting apparatus 41 can output the position information of the target region L and the diagnosis assisting information C indicating the degree of seriousness of the target region L not to interfere with the observation of the endoscope image X during the diagnosis by the operator and can assist with the diagnosis.

Second Embodiment

The first period and the second period start at the same time in the first embodiment, but the first period may start after the end of the second period.

Figure 6:
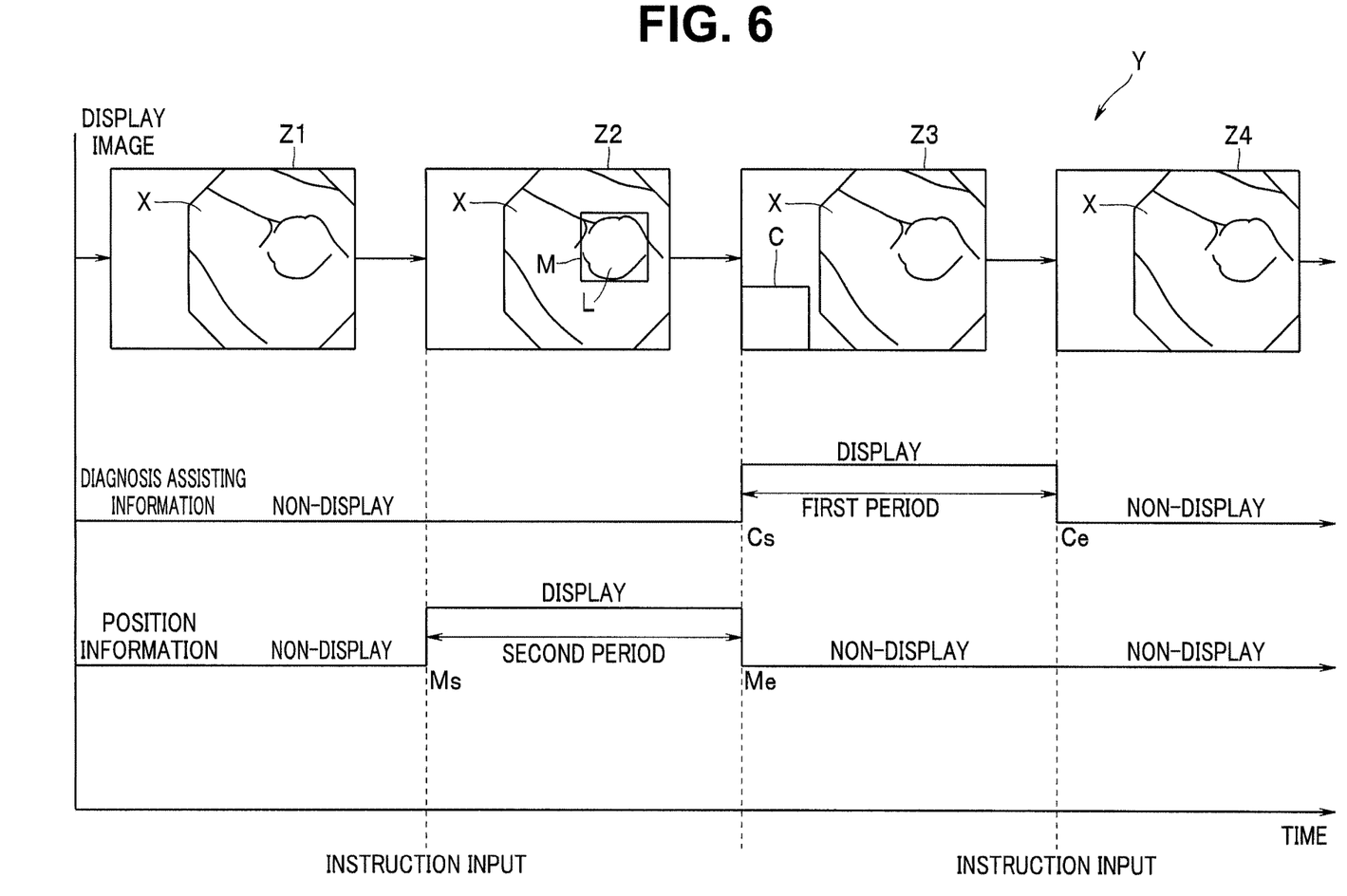
FIG. 6 is an explanatory diagram illustrating an example of a transition of a display image of a diagnosis assisting apparatus according to a second embodiment of the present invention.

FIG. 6 is an explanatory diagram showing an example of a transition of a display image Y of a diagnosis assisting apparatus according to a second embodiment of the present invention. In the present embodiment, the same components as the components of the other embodiment will not be described.

A second period end determination portion Q1e (two-dotted chain line in FIG. 3) determines whether a second period ends. When the second period end determination portion Q1e determines that the second period ends, a first setting portion Q1 starts a first period.

An instruction input determination portion Q1c determines based on an instruction signal inputted from an operation section 31 whether any instruction to start or end an information display exists. When the instruction input determination portion Q1c determines that an instruction signal to start the information display exists, a second setting portion Q2 sets a second start time point Ms with predetermined control information, and starts a second period. On the other hand, when instruction input determination portion Q1c determines that an instruction signal to end the second period exists, the second setting portion Q2 sets a second end time point Me with predetermined control information, and ends the second period.

Display images Z1 and Z4 shown in FIG. 6 are equal to the display image Y1, and thus will not be described.

When the operator inputs an instruction to start an information display through the operation section 31, the instruction input determination portion Q1c determines that the instruction to start the information display is inputted, and the second setting portion Q2 sets the start of the second period. The display control section 43 displays a mark M on the display image Z2 from the second start time point Ms.

At the second end time point Me, when the second period ends, the second period end determination portion Q1e determines that the second period ends. When the second period end determination portion Q1e determines that the second period ends, the first setting portion Q1 sets the start of the first period. The display control section 43 displays a diagnosis assisting information C at the start of the first period, and does not display the mark M at the end of the second period. A display image Z3 shows an example in which the diagnosis assisting information C is displayed and the mark M is not displayed.

In the endoscope system Es, when the target region L is detected, the mark M is displayed on the endoscope image X. Subsequently, in the endoscope system Es, the mark M is not displayed and the diagnosis assisting information C is displayed. Thus, the operator can grasp the position of the target region L from the mark M on the endoscope image, and can proceed with the diagnosis. Subsequently, the operator can visually observe the target region L in which the mark M is not displayed, can grasp the degree of seriousness of the target region L from the diagnosis assisting information C, and can proceed with the diagnosis.

According to the second embodiment, the diagnosis assisting apparatus 41 can output the position information of the target region L and the diagnosis assisting information C indicating the degree of seriousness of the target region L not to interfere with the observation of the endoscope image X during the diagnosis by the operator and can assist with the diagnosis.

In the embodiments, the period setting portion P3 includes the continuation determination portion Q1a, the treatment instrument determination portion Q1b, the instruction input determination portion Q1c, the extension determination portion Q1d, the second period end determination portion Q1e, the degree-of-seriousness determination portion Q2a, the size determination portion Q2b, the number determination portion Q2c, the motion determination portion Q2d, and the treatment operation determination portion Q2e, but may be configured to include some of these components.

In the embodiments, one display section 51 is provided, but a plurality of display sections 51 may be provided. For example, when two display sections 51 are provided, one may be the first region A1 and the other may be the second region A2.

In the description of the operations of the embodiments, the start and the end of the information display are performed according to the instruction input from the operator, but may be performed according to the detection of the target region L by the detection portion P1. For example, in the first embodiment, the period from the start to the end of the detection of the target region L by the detection portion P1 may be set as the first period. For example, in the second embodiment, the second period may start in response to the start of the detection of the target region L by the detection portion P1, and the first period may end in response to the non-detection of the target region L.

In the first embodiment, the first period and the second period are performed at the same time, but may be performed separately. For example, the first period may start before the second period, or the second period may start before the first period.

In the second embodiment, the first period starts in response to the end of the second period, and a period during which the first period and the second period overlap with each other does not exist. As long as the first period has a period that does not overlap with the second period, the period during which the first period and the second period overlap with each other may exist.

In the embodiments, the first period ends after the second period, but the second period may end after the first period as long as the first period has the period that does not overlap with the second period. For example, when the first period starts before the second period, the second period may end after the first period.

Note that the steps in each procedure in the embodiments may be executed in a different execution order, may be simultaneously executed, or may be executed in a different order at each execution, without losing the characteristics of the procedure. In addition, all or part of the steps of each procedure in the embodiment may be achieved by hardware. For example, all or some of the detection portion P1, the classification portion P2, and the period setting portion P3 may be configured by a hardware circuit instead of a software circuit.

The present invention is not limited to the above-described embodiments, but, for example, various kinds of changes and modifications are applicable without departing from the gist of the present invention.

What is claimed is:

1. A diagnosis assisting apparatus comprising:
   a processor configured to
     detect at least one target region from an acquired image and output position information of the target region,
     classify the target region based on a predetermined classification condition corresponding to a diagnosis index and output diagnosis assisting information indicating a degree of seriousness of the target region, and
     control a display image such that a first period, during which the diagnosis assisting information is displayed, has a period that does not overlap with a second period, during which the position information is superimposed on the image and is displayed;
   wherein the processor controls the display image such that the diagnosis assisting information is displayed in a first region different from a region in which the image is displayed; and
   the processor sets the first period and sets the second period according to setting of the first period.

2. The diagnosis assisting apparatus according to claim 1, wherein the processor sets a start of the first period when the second period ends.

3. The diagnosis assisting apparatus according to claim 1, wherein
   the processor sets the second period according to the setting of the first period and the diagnosis assisting information.

4. The diagnosis assisting apparatus according to claim 3, wherein the processor sets the second period according to the degree of seriousness.

5. The diagnosis assisting apparatus according to claim 4, wherein the processor is configured to
   output the diagnosis assisting information having a probability of an adenomatous lesion and a probability of a non-adenomatous lesion,
   determine based on the probability of whether the target region is either the adenomatous lesion or the non-adenomatous lesion, and
   set the second period longer when the target region is determined to be the non-adenomatous lesion than when the target region is determined to be the adenomatous lesion.

6. The diagnosis assisting apparatus according to claim 1, wherein the processor is configured to
   determine whether a difference between an end time point of the first period and an end time point of the second period is smaller than a predetermined difference, and
   extend the first period by a predetermined extension time when the difference is determined to be smaller than the predetermined difference.

7. The diagnosis assisting apparatus according to claim 1, wherein the processor is configured to set the first period and the second period such that the second period ends before the first period.

8. A non-transitory computer-readable storage medium in which a program is stored, the program including:
   a code configured to detect a target region from an acquired image and output position information of the target region;
   a code configured to classify the target region based on a predetermined classification condition corresponding to a diagnosis index and output diagnosis assisting information indicating a degree of seriousness of the target region; and
   a code configured to control a display image such that a first period, during which the diagnosis assisting information is displayed in a first region, has a period that does not overlap with a second period, during which the position information is superimposed on the image in a second region and is displayed;
   wherein the display image is controlled such that the diagnosis assisting information is displayed in the first region different from the second region in which the image is displayed; and
   the first period is set and the second period is set according to setting of the first period.

9. A diagnosis assisting method comprising:
   detecting a target region from an acquired image and outputting position information of the target region;
   classifying the target region based on a predetermined classification condition corresponding to a diagnosis index and outputting diagnosis assisting information indicating a degree of seriousness of the target region; and
   controlling a display image such that a first period, during which the diagnosis assisting information is displayed in a first region, has a period that does not overlap with a second period, during which the position information is superimposed on the image in a second region and is displayed;
   wherein the display image is controlled such that the diagnosis assisting information is displayed in the first region different from the second region in which the image is displayed; and the first period is set and the second period is set according to setting of the first period.

10. A diagnosis assisting apparatus comprising:
a processor configured to:
detect at least one target region from an acquired image and output position information of the target region;
classify the target region based on a predetermined classification condition corresponding to a diagnosis index and output diagnosis assisting information indicating a degree of seriousness of the target region; and
set a first period and a second period based on the acquired image such that the first period, during which the diagnosis assisting information is displayed, has a period that does not overlap with the second period during which the position information is superimposed on the image and is displayed, and control a display image.

11. The diagnosis assisting apparatus according to claim 10, wherein the processor is configured to set the first period and the second period according to a detection result of the target region from the image.

12. The diagnosis assisting apparatus according to claim 10, wherein the processor sets a period, during which the target region is continuously detected, as the first period.

13. The diagnosis assisting apparatus according to claim 10, wherein the processor sets an end of the first period when a treatment instrument is detected in the image.

14. The diagnosis assisting apparatus according to claim 10, wherein the processor sets at least one of a start and an end of the first period in response to an instruction input from an operator.

15. The diagnosis assisting apparatus according to claim 10, wherein the processor is configured to
detect a size of the target region,
determine the size, and
set the second period according to a determination result of the size.

16. The diagnosis assisting apparatus according to claim 15, wherein the processor is configured to
determine whether the size is smaller than a predetermined size, and
set the second period longer when the size is determined to be smaller than the predetermined size than when the size is determined to be larger than the predetermined size.

17. The diagnosis assisting apparatus according to claim 16, wherein the processor is configured to
output the diagnosis assisting information having a probability of an adenomatous lesion and a probability of a non-adenomatous lesion,
determine based on the probability whether the target region is either the adenomatous lesion or the non-adenomatous lesion, and
set the second period longer when the target region is the adenomatous lesion and the size is determined to be smaller than the predetermined size than when the size is determined to be larger than the predetermined size.

18. The diagnosis assisting apparatus according to claim 15, wherein the processor is configured to
determine whether the size is equal to or smaller than 5 mm, and
set the second period when the size is determined to be equal to or smaller than 5 mm.

19. The diagnosis assisting apparatus according to claim 10, wherein the processor is configured to set the second period according to a number of target regions.

20. The diagnosis assisting apparatus according to claim 19, wherein the processor configured to
determine whether the number of the target regions is greater than a predetermined number, and
set the second period longer when the number of the target regions is determined to be greater than the predetermined number than when the number of target regions is determined to be smaller than the predetermined number.

21. The diagnosis assisting apparatus according to claim 19,
wherein the processor sets the second period such that the second period is different for each of the target regions when the number of the target regions is plural.

22. The diagnosis assisting apparatus according to claim 10, wherein the processor is configured to
determine a motion direction and a motion amount of the target region in the image, and
set the second period according to the motion direction and the motion amount.

23. The diagnosis assisting apparatus according to claim 22, wherein the processor is configured to
determine whether the motion amount is larger than a predetermined amount, and
set the second period longer when the motion amount is determined to be larger than the predetermined amount than when the motion amount is determined to be smaller than the predetermined amount.

24. The diagnosis assisting apparatus according to claim 22, wherein the processor is configured to set the second period longer when the motion direction is determined to be a direction toward a center of the image than when the motion direction is determined to be a direction toward an outside of the image.

25. The diagnosis assisting apparatus according to claim 10, wherein the processor is configured to
determine whether a predetermined treatment operation of the treatment instrument is performed, and
set an end of the second period when the predetermined treatment operation is determined to be performed.

26. A non-transitory computer-readable storage medium in which a program is stored, the program including:
a code configured to detect at least one target region from an acquired image and output position information of the target region;
a code configured to classify the target region based on a predetermined classification condition corresponding to a diagnosis index and output diagnosis assisting information indicating a degree of seriousness of the target region; and
a code configured to set a first period and a second period based on the acquired image such that the first period, during which the diagnosis assisting information is displayed, has a period that does not overlap with the second period during which the position information is superimposed on the image and is displayed, and control a display image.

27. The non-transitory computer-readable storage medium according to claim 26, wherein the code is configured to set the first period and the second period according to a detection result of the target region from the image.

28. A diagnosis assisting method comprising:
detecting at least one target region from an acquired image and output position information of the target region;
classifying the target region based on a predetermined classification condition corresponding to a diagnosis index and outputting diagnosis assisting information indicating a degree of seriousness of the target region; and setting a first period and a second period based on the acquired image such that the first period, during which the diagnosis assisting information is displayed, has a period that does not overlap with the second period during which the position information is superimposed on the image and is displayed, and controlling a display image.

29. The diagnosis assisting method according to claim 28, wherein the first period and the second period are set according to a detection result of the target region from the image.

\* \* \* \* \*